US008883510B2

(12) United States Patent
Gehring et al.

(10) Patent No.: US 8,883,510 B2
(45) Date of Patent: Nov. 11, 2014

(54) THROMBOCYTE FUNCTION DETERMINATION METHOD USING A RESONATOR

(75) Inventors: Frank K. Gehring, Obernheim (DE); Hans Wendel, Balingen (DE); Stefan Sinn, Herrenberg (DE); Lothar Mueller, Wiesbaden (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 81 days.

(21) Appl. No.: 13/394,550

(22) PCT Filed: Sep. 9, 2010

(86) PCT No.: PCT/EP2010/005548
§ 371 (c)(1),
(2), (4) Date: Jul. 6, 2012

(87) PCT Pub. No.: WO2011/029600
PCT Pub. Date: Mar. 17, 2011

(65) Prior Publication Data
US 2012/0270326 A1    Oct. 25, 2012

(30) Foreign Application Priority Data
Sep. 9, 2009  (DE) .................... 10 2009 040 881

(51) Int. Cl.
*G01N 29/44*   (2006.01)
*G01N 33/48*   (2006.01)
*G01N 33/86*   (2006.01)
*G01N 29/036*  (2006.01)

(52) U.S. Cl.
CPC .............. *G01N 29/036* (2013.01); *G01N 33/86* (2013.01); *G01N 2291/0256* (2013.01)
USPC .................. 436/69; 436/63; 435/7.1; 435/29; 73/64.42; 73/64.53

(58) Field of Classification Search
USPC ............. 436/63, 69, 501, 536; 422/73; 435/2, 435/6.1, 7.1, 13, 29, 34; 73/64.41, 64.42, 73/64.53; 600/369
See application file for complete search history.

(56) References Cited

U.S. PATENT DOCUMENTS

| | | | | |
|---|---|---|---|---|
| 4,246,344 | A * | 1/1981 | Silver, III ........................ | 435/39 |
| 4,695,956 | A * | 9/1987 | LeVeen et al. .................. | 435/13 |
| 6,046,051 | A   | 4/2000 | Jina | |
| 7,207,222 | B2 * | 4/2007 | Thompson et al. ............. | 73/590 |
| 2005/0015001 | A1 | 1/2005 | Lec et al. | |
| 2008/0261261 | A1 * | 10/2008 | Grimes et al. .................. | 435/29 |

FOREIGN PATENT DOCUMENTS

| | | |
|---|---|---|
| JP | H06-308130 | 11/1994 |
| JP | 08085726 | 4/1996 |
| JP | H08-85726 | 4/1996 |
| WO | 9101383 A1 | 2/1991 |
| WO | 2009075891 A2 | 6/2009 |

OTHER PUBLICATIONS

European Patent and Trademark Office, Office Action, December 12, 2012, pp. 1-3, File No. 10760912.5-1240, Applicant: Andreas Hettich GmbH & Co.
German Patent and Trademark Office, Office Action, March 19, 2012, pp. 1-8, File No. 102009040881.9, Applicant: Andreas Hettich GmbH &Co. KG, Munich, Germany.
Takehisa Matsuda et al.: Novel instrumentation monitoring in situ platelet adhesivity with a quartz crystal microbalance, ASAIO, Hagerstown, MD, US, vol. 28, No. 3, Jul. 1, 1992, pp. 171-173, XP000321538, ISSN 1058-2916.
Real-time monitoring of adhesion and aggregation of platelets using thickness shear mode (TSM) sensor, Ergezen, Appel, Shah, Kresh, Lee, Wootton, Biosensors and Bioelectronics 23 575-582, Jul. 31, 2007.
A new method for continuous measurement of platelet adhesion under flow conditions; Nagai, Handa, Ikeda, Kawakami, Harada, Sakasita, ASAIO, Journal 1993, M558-560.
International Search Report, PCT/EP2010,005548, Dec. 8, 2010, European Patent Office.
Written Opinion, PCT/EP2010,005548, Dec. 8, 2010, European Patent Office.
European Patent Office, Office Action, Jul. 22, 2013, pp. 1-18, Application No. 10760912.5-1559, Applicant: Andreas Hettich GmbH & Co. KG.
Japanese Patent Office, Office Action, Notice of Reasons for Rejection, Mar. 10, 2014, Japanese Application No. 2012-528272, pp. 1-7, Japan.
European Patent Office, Office Action, Jan. 23, 2014, Application No. 13196301.9-1559, Applicant: Andreas Hettich GmbH & Co. KG, pp. 1-4.
Matsuda et al, Novel Instrumentation Monitoring in Situ Platelet Adhesivity With a Quartz Crystal Microbalance, ASAIO Journal, 1992, pp. 171-173.
Pogliani et al, Platelet Dysfunction in Acute Megakaryoblastic Leukemia, Acta Haemat, 1989, vol. 81, No. 1, pp. 1-4.
Welle et al, Competitive Protein Adsorption on Micro Patterned Polymeric Biomaterials, and Viscoelastic Properties of Tailor Made Extracellular Matrices, Biomolecular Engineering, Feb. 9, 2007, vol. 24, No. 1, pp. 87-91.

* cited by examiner

*Primary Examiner* — Maureen Wallenhorst
(74) *Attorney, Agent, or Firm* — Woodling, Krost and Rust

(57) ABSTRACT

The invention relates to a method for determining haemostasis parameters by measuring vibration parameters of a resonator having a measuring surface which contacts a platelet containing sample fluid. The invention is characterized by the analysis of the characteristic of a vibration parameter over time, based on which the platelet function will then be assessed and a distinction will be made between the presence of an adhesion disorder or that of an aggregation disorder.

15 Claims, 1 Drawing Sheet

THROMBOCYTE FUNCTION DETERMINATION METHOD USING A RESONATOR

This application is the national phase entry of PCT/EP2010/005548. This application claims the benefit and priority of and to PCT/EP2010/005548, international application filing date Sep. 9, 2010, which claims the benefit and priority of and to German patent application no. DE 10 2009 040 881.9, filed Sep. 9, 2009. Further, PCT/EP2010/005548 and German patent application no. DE 10 2009 040 881.9 are hereby incorporated herein by reference hereto.

The invention relates to a method for the determination of thrombocyte function.

To enable coagulation, both primary and secondary haemostases need to be fully functional. Various ways of testing secondary haemostasis have already been known. However, for primary haemostasis, which can be subdivided into thrombocyte adhesion and aggregation, no sufficiently precise analysis method for determining the specific thrombocyte function has as yet been described in the prior art.

According to the prior art, blood analyses for testing haemostasis are possible. However, these tests cannot be used to determine whether it is the adhesion or the aggregation step of primary haemostasis that is dysfunctional or, in which way aggregation is inhibited.

It is known that blood platelets can be made to adsorb to the surface of a vibrating quartz crystal through adhesion. While the quality of such an adsorption can be measured, any dysfunctional aggregation cannot be specifically identified by such measurement.

Described in the publication entitled "Real-Time Monitoring of Adhesion and Aggregation of Platelets using Thickness Shear Mode Sensors" is an analysis of the coagulation phases of blood platelet adhesion and aggregation, for which purpose a vibrating quartz crystal is used. As is explained in this document, the quality of the different phases, adhesion and aggregation, can be detected by means of a vibrating quartz crystal. However, it does not solve the problem of testing thrombocyte functionality as regards adhesion and aggregation. It is known from this printed document that proper aggregation can be distinguished quite well from insufficient platelet adhesiveness as successful aggregation will result in a high frequency and/or damping change. Similarly, it is known to determine the platelet aggregation capability. However, this method does not allow a reliable distinction to be made between the thrombocytes adhesion and aggregation capabilities as the frequency deviation does not only depend on the addition of ADP but also on the concentration of the thrombocytes, the binding strength of the vibrating quartz crystal surface and the adhesiveness of the thrombocytes. Consequently, a false positive decision may be made as this method can merely determine whether or not a frequency drop has occurred, and the adhesion of the thrombocytes alone may already cause a strong frequency drop under certain conditions. Also U.S. 2005/0015001 A1 basically describes what has been set out above.

The printed document entitled "A New Method for Continuous Measurement of Platelet Adhesion under Flow Conditions" discloses that platelet adhesion can be measured but does not relate such measurement to the analysis of a dysfunction or to combining it with an assessment of the aggregation function.

Sheet 24 of the lecture entitled [translated from German] "Potential of Vibrating Quartz Crystal Sensors for Inline Haemostasis Testing" shows two frequency curves which are to allow an assessment of the thrombocyte function. One illustration thereof shows a frequency drop during the vibrating quartz crystal measurement of activated blood, the second curve shows no frequency drop in the case of inhibited blood. This is merely another way of stating that a function can be derived from the behaviour of the vibration parameters. However, these documents do not indicate whether the stated function illustrates adhesion, aggregation or any other kind of adsorption of a substance to the surface of the vibrating quartz crystal. No distinct function assignment may be gathered from this disclosure.

It is the object of the invention to provide a method which allows a statement to be made as to which branch of cellular coagulation is defective.

In a known manner, the vibration parameters of a resonator are measured for determining primary haemostasis parameters. A surface of said resonator contacts a sample fluid containing thrombocytes. This will cause thrombocytes or other blood components to be adsorbed to the surface of the vibrating quartz crystal which will affect its vibration behaviour.

According to the invention, for determining the thrombocyte function, a sample fluid is applied to a resonator surface and an analysis of the characteristic and/or kinetics of the one or plural vibration parameters is performed, which is then used as a basis for assessing the thrombocyte function. Based on this characteristic, a distinction will then be made between a total dysfunction, or a disorder of platelet adhesion or aggregation. For this purpose, the characteristic of the curve of the vibration parameters over time is assessed and in view of the assessment, a statement will be made as to which cellular coagulation branch is defective. This method allows a diagnostic investigation using a resonator.

This is very advantageous since precise adjustment of the corresponding medication will be possible once it has been established which coagulation branch is defective. Generally, these examination methods provide a vast information pool regarding cellular coagulation. Well-aimed medication clearly reduces side effects for the patient and allows significant cost savings.

Generally, in a first embodiment of the invention, the vibration parameters are analysed on the basis of the resonance frequency. Alternatively, it is also possible to analyse resonator damping and/or amplitude. In particular, the fundamental oscillation is examined for this purpose.

After starting the measurement, a sample fluid containing platelets is applied to the vibrating quartz crystal. If there is no change in the curve of the vibration over time, then the thrombocyte function shall be assumed to be defective. This means that the platelets are incapable of adhering to the surface. As a result, aggregation will also be impossible. No further examination will be required since no blood clotting will occur where adhesion is impossible. This dysfunction thus corresponds to an adhesion disorder.

In contrast, if the vibration parameters drop in a more or less linear manner over time, the conclusion is that the platelets are basically capable of adhesion. Adhesion can be prevented by adding an inhibitor. Adhesion will be prevented by blocking the GPIIb/IIIa receptor, for example. It is thus possible, once a sample has tested positive for its adhesiveness, to repeat the test with an artificially inhibited platelet function so as to verify the result.

According to this method, the thrombocytes contained in a non-activated sample fluid which is applied to a vibrating quartz crystal will be assessed as capable of adhesion based on the drop of vibration parameters.

For an examination of the aggregation capability of the platelets contained in the sample fluid, the latter will first have to be activated. Activation of the sample is performed by adding an activator. The activator may either be added shortly before application of the sample, or the vibrating quartz crystal already includes an activator incorporated into its surface. According to this method, the vibration parameter is also recorded over time in this case. If a very sharp drop of the vibration parameters over time, for example of the exponential type, is detected, the thrombocytes will be found to be capable of aggregation.

If the vibration behaviour of the vibrating quartz crystal with the activated sample is identical to that of the non-activated sample, then the thrombocytes will be found capable of adhesion but incapable of aggregation. The diagnosis will be an aggregation disorder.

Furthermore, by adding various activators, it can be determined which platelet receptor is dysfunctional. The various activation pathways may thus be triggered by the addition of e.g. van Willebrand factor (vWF), arachidonic acid (AA), adenosine disphosphate (ADP) or fibrinogen which allows narrowing down the dysfunction of the corresponding activation pathways.

Such narrowing down may also be accomplished in that different receptors are blocked in a successful platelet aggregation. If all the receptors are blocked except one that is to be examined, it can be established whether this receptor is defective by measuring the aggregation behaviour of the activated sample and, if the curve of the vibration parameters suggests adhesion, the unblocked receptor can be considered defective.

In particular, activating and blocking individual receptors will allow the identification of dysfunctional receptors. Furthermore, blocking or activating individual groups of receptors by a specific antibody or parts thereof is also envisaged. Moreover, this function may also be accomplished by other specifically binding molecules such as lectins or nucleic acid fragments.

It will also prove advantageous if an activator such as fibrinogen has already been incorporated into the surface of a vibrating quartz crystal for example. This avoids the problem of having to keep the time period from sample activation to the actual measurement as short as possible for which reason the entire apparatus can be made of a simpler design. The platelets will thus be activated as they adhere to the fibrinogen layer, which will then trigger aggregation.

Further advantages, features and possible applications of the present invention will become obvious from the description which follows, in combination with the embodiments illustrated in the drawings. The invention will now be described in more detail with reference to the drawings.

Figure 1:
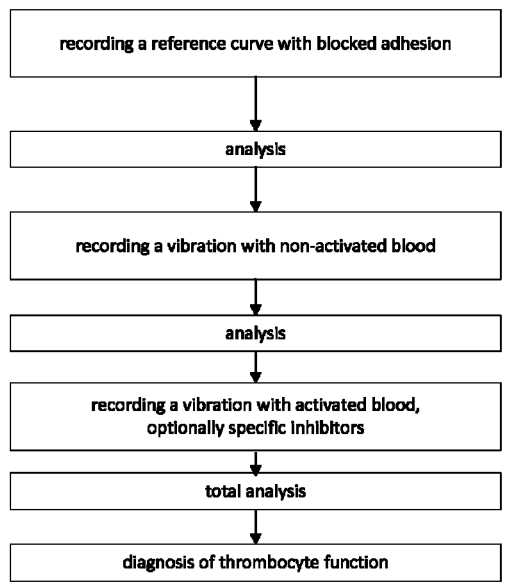
FIG. 1 is a flow chart of a method for determining platelet function.

FIG. 1 is a flow chart of a method for determining platelet function in a blood sample. First, platelets that have not been activated and whose adhesiveness has been blocked will be applied to a vibrating quartz crystal. Adhesiveness can be inhibited artificially by for example blocking the collagen receptor or the GPIb-IX receptor by Abciximab. This will prevent platelet adhesion to the vibrating quartz crystal surface, resulting in an unaffected reference curve of the resonance frequency.

After recording the reference curve, a further sample fluid will either be applied to the same vibrating quartz crystal or to the cleansed vibrating quartz crystal. This sample fluid will contain platelets whose receptors have neither been blocked nor activated regarding adhesion. Subsequently, the curve will be analysed. If there is a sharper drop of the resonance frequency over time than was the case with the sample containing the inhibited adhesion receptors, then the platelets in the sample fluid will be considered capable of adhesion, and a further measurement step will follow.

In a further step, a sample fluid induced using an activator, for example adenosine diphosphate (ADP), van Willebrand Factor (vWF) or another factor will be applied to the vibrating quartz crystal surface. If a sharper drop of the resonance frequency over time is observed than was the case in the previous step, this will imply, if fibrinogen activation was used, that primary aggregation is functional. In a further step, an activator or a sample induced with an activator will then be added which will trigger secondary aggregation.

If the resonance frequency drop is clearly sharper than before, secondary aggregation will also be considered functional. If the addition of respective activators does not affect the vibration behaviour of the resonator, the corresponding receptors can be assumed to be dysfunctional.

This flow defines a general procedure which consists in first measuring an inhibited sample, then a non-activated sample and subsequently an activated sample, with a random number of rinsing steps in between. Moreover, this also allows several combinations of inhibition and activation steps to be included in this procedure.

This allows the precise determination of be defective cellular coagulation branch.

Figure 2:
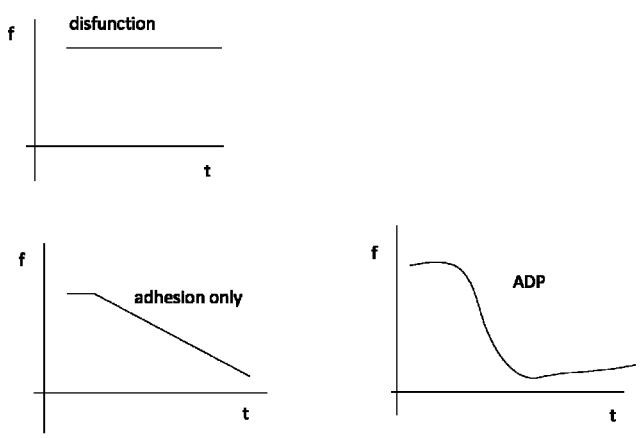
FIG. 2 is a schematic view of the respective course of vibration parameters in the case of dysfunction, adhesion and aggregation.

FIG. 2 shows three frequency curves of the vibrating quartz crystal over time, each of a different platelet function. The first frequency curve is straight over the entire time. No frequency drop can be found in this case. This means that no or only a negligible number of platelets will be adsorbed to the vibrating quartz crystal surface. Such a frequency curve is a clear indication of a platelet dysfunction. Possibly, adsorption to the vibrating quartz crystal surface has also been prevented by deliberate blocking by means of Abciximab addition. The platelets are incapable of adhering to the surface, either due to a dysfunction or because they were deliberately inhibited using Abciximab, for example.

The second graph shows a linear frequency decrease over time. This shows that an increasing number of platelets and other blood components are gradually becoming adsorbed to the vibrating quartz crystal surface. It can clearly be concluded from such a frequency curve that adhesion is taking place.

The third graph shows a sharp frequency drop. Such a curve indicates the presence of functional platelets which have at least one functional receptor for aggregation. For aggregation, the blood will first have to be activated. Such may be triggered by means of adenosine diphosphate (ADP), fibrinogen or van Willebrand Factor (vWF). Activation can also be achieved by means of arachidonic acid (AA). Depending on the activator used and/or any selective inhibitor possibly used, this will allow verification of the functionality of the individual platelet receptors.

The invention claimed is:

1. A method for determining an adhesion disorder or an aggregation disorder, comprising the steps of:
   activating a platelet-containing sample fluid;
   measuring a vibration parameter of a resonator with respect to time, said resonator having a measuring surface, and, said measuring surface contacts said platelet-containing sample fluid;
   recording said vibration parameter with respect to time;

analyzing a characteristic curve of said recorded vibration parameter with respect to time;

determining platelet function based on said analysis of said characteristic curve of said recorded vibration parameter, said platelet function includes the adhesion of platelets and the aggregation of platelets;

said step of analyzing said characteristic curve includes determining if said vibration parameter is unchanged with respect to time indicating an absolute platelet dysfunction in regard to both adhesion and aggregation;

said step of analyzing said characteristic curve includes determining if said vibration parameters change substantially exponentially with respect to time indicating that said platelets are considered functional in regard to aggregation;

said step of analyzing said characteristic curve includes determining if said vibration parameters change substantially linearly with respect to time indicating that said platelet function is dysfunctional in regard to aggregation but is functional in regard to adhesion; and, determining, based on said step of analyzing said characteristic curve, the presence of an adhesion disorder or an aggregation disorder.

2. The method as claimed in claim 1, wherein said vibration parameter is the resonance frequency of said measuring surface of said resonator.

3. The method as claimed in claim 1, wherein damping and/or amplitude of said resonator is used as the vibration parameter.

4. The method as claimed in claim 1 wherein said platelet function will be determined in more detail by adding different activators which will trigger different activation branches.

5. The method as claimed in claim 4 wherein said activation branches will be blocked by the addition of respective inhibitors.

6. The method as claimed in claim 5 wherein activating and blocking individual receptors will allow identification of receptors that exhibit functional defects.

7. The method as claimed in claim 5 wherein blocking or activating individual receptors or groups of receptors will be achieved through a specific antibody, parts thereof, or through other specifically binding molecules; and, said binding molecules include lectins, and, fragments of nucleic acids.

8. The method as claimed in claim 4 wherein activating and blocking individual receptors will allow identification of receptors that exhibit functional defects.

9. The method as claimed in claim 4 wherein blocking or activating individual receptors or groups of receptors will be achieved through a specific antibody, parts thereof, or through other specifically binding molecules; and, said binding molecules include lectins, and, fragments of nucleic acids.

10. A method for determining an adhesion disorder or an aggregation disorder, comprising the steps of:

measuring a vibration parameter of a resonator with respect to time, said resonator having a measuring surface, and, said measuring surface contacts a platelet-containing sample fluid, said platelet-containing sample fluid being a non-activated platelet-containing sample fluid;

recording said vibration parameter with respect to time;

analyzing a characteristic curve of said recorded vibration parameter with respect to time;

determining platelet function based on said analysis of said characteristic curve of said recorded vibration parameter, said platelet function includes the adhesion of platelets and the aggregation of platelets;

said step of analyzing said characteristic curve includes determining if said vibration parameter is unchanged with respect to time indicating an absolute platelet dysfunction in regard to both adhesion and aggregation;

said step of analyzing said characteristic curve includes determining if said vibration parameters change substantially linearly with respect to time indicating that said platelet function is dysfunctional in regard to aggregation but is functional in regard to adhesion;

activating said platelet-containing sample fluid;

measuring a vibration parameter of a resonator with respect to time, said resonator having a measuring surface, and, said measuring surface contacts said activated platelet-containing sample fluid;

recording said vibration parameter with respect to time in regard to said activated platelet-containing sample fluid;

analyzing a characteristic curve of said recorded vibration parameter with respect to time in regard to said activated platelet-containing sample fluid;

determining platelet function based on said analysis of said characteristic curve of said recorded vibration parameter with respect to time in regard to said activated platelet-containing sample fluid, said platelet function includes the adhesion of platelets and the aggregation of platelets;

said step of analyzing said characteristic curve of said recorded vibration parameter with respect to time in regard to said activated platelet-containing sample fluid includes determining if said vibration parameters change substantially exponentially with respect to time indicating that said platelets are considered functional in regard to aggregation; and, determining, based on said step of analyzing said characteristic curve, the presence of an adhesion disorder or an aggregation disorder.

11. The method as claimed in claim 10, wherein said vibration parameter is the resonance frequency of said measuring surface of said resonator.

12. The method as claimed in claim 11, wherein the platelets will be considered capable of adhesion if there is a change of the vibration parameter with respect to time of said non-activated sample fluid.

13. The method as claimed in claim 10, wherein said vibration parameter is damping and/or amplitude of said resonator.

14. The method as claimed in claim 13, wherein said platelets will be considered capable of adhesion if there is a change of the vibration parameter with respect to time of said non-activated sample fluid.

15. The method as claimed in claim 10, wherein said platelets will be considered capable of adhesion if there is a change of the vibration parameter with respect to time of said non-activated sample fluid.

* * * * *